US009868685B2

(12) United States Patent
Fritz et al.

(10) Patent No.: US 9,868,685 B2
(45) Date of Patent: *Jan. 16, 2018

(54) PROCESSING BY A SEPARATION TECHNIQUE OF A GAS MIXTURE FORMED FROM A PRODUCT STREAM OF A DIMETHYL REACTOR

(71) Applicant: Linde Aktiengesellschaft, München (DE)

(72) Inventors: Helmut Fritz, München (DE); Andreas Peschel, Wolfratshausen (DE)

(73) Assignee: LINDE AKTIENGESELLSCHAFT, München (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/110,037

(22) PCT Filed: Jan. 7, 2015

(86) PCT No.: PCT/EP2015/050166
§ 371 (c)(1),
(2) Date: Jul. 6, 2016

(87) PCT Pub. No.: WO2015/104290
PCT Pub. Date: Jul. 16, 2015

(65) Prior Publication Data
US 2016/0326081 A1  Nov. 10, 2016

(30) Foreign Application Priority Data
Jan. 7, 2014 (EP) .................... 14000042

(51) Int. Cl.
| | |
|---|---|
| *C07C 41/42* | (2006.01) |
| *B01D 3/14* | (2006.01) |
| *B01D 53/14* | (2006.01) |
| *C07C 41/01* | (2006.01) |
| *C07C 41/38* | (2006.01) |
| *B01D 5/00* | (2006.01) |

(52) U.S. Cl.
CPC .............. *C07C 41/42* (2013.01); *B01D 3/143* (2013.01); *B01D 5/0036* (2013.01); *B01D 53/1431* (2013.01); *B01D 53/1493* (2013.01); *C07C 41/01* (2013.01); *C07C 41/38* (2013.01); *B01D 2257/108* (2013.01); *B01D 2257/502* (2013.01); *B01D 2257/504* (2013.01); *Y02P 20/152* (2015.11); *Y02P 70/34* (2015.11)

(58) Field of Classification Search
None
See application file for complete search history.

(56) References Cited

U.S. PATENT DOCUMENTS

| | | |
|---|---|---|
| 4,536,485 A | 8/1985 | Topp-Jorgensen |
| 5,189,203 A | 2/1993 | Hansen et al. |
| 5,908,963 A | 6/1999 | Voss et al. |
| 2009/0156698 A1 | 6/2009 | Rostrup-Nielsen et al. |
| 2016/0332945 A1 * | 11/2016 | Fritz ...................... C07C 41/42 |

OTHER PUBLICATIONS

PCT/EP2015/050166 English Translation of the International Search Report & Written Opinion dated Mar. 11, 2015, 10 pages.
Fang D., et al: "Preparation of dimethyl ether involves condensing reaction product, absorption, rectification of dimethyl ether, rectification of methanol, and preparation of dimethyl ether by dehydrating methanol" WPI / Thomson,, vol. 2010, No. 9, Dec. 23, 2009.

* cited by examiner

*Primary Examiner* — Rosalynd A Keys
(74) *Attorney, Agent, or Firm* — Lathrop Gage LLP

(57) ABSTRACT

A method for the processing, by separation technology, of a gas mixture (k) which is formed from a product stream (d) of a reactor (4) for synthesizing dimethyl ether from synthesis gas (b), and which contains at least dimethyl ether, carbon dioxide and at least one other component which is lower-boiling than carbon dioxide, is proposed. The gas mixture (k) is cooled at a first pressure level from a first temperature level to a second temperature level and a fraction of the gas mixture (k) that remains in gaseous form at the second temperature level is washed in an absorption column (16) with a reflux (v) predominantly containing carbon dioxide. The reflux (v) predominantly containing carbon dioxide is at least partially formed from a fraction of the gas mixture (k) which is separated in liquid form during the cooling.

12 Claims, 2 Drawing Sheets

PROCESSING BY A SEPARATION TECHNIQUE OF A GAS MIXTURE FORMED FROM A PRODUCT STREAM OF A DIMETHYL REACTOR

The invention relates to a method for the separation technology processing of a gas mixture which is formed from a product stream of a reactor for synthesising dimethyl ether from synthesis gas.

PRIOR ART

Dimethyl ether (DME) is the structurally simplest ether. Dimethyl ether contains two methyl groups as organic residues. Dimethyl ether is polar and is conventionally used in liquid form as a solvent. Dimethyl ether can also be used as a refrigerant and replace conventional chlorofluorocarbons.

Recently, dimethyl ether has increasingly been used as a substitute for fuel gas (liquid gas) and conventional fuels such as diesel. Because of its comparatively high cetane number of 55 to 60, conventional diesel engines, for example, need to be only slightly modified in order to run on dimethyl ether. Dimethyl ether burns comparatively cleanly without forming carbon deposits. If dimethyl ether is produced from biomass, it counts as a so-called biofuel and can therefore be marketed on favourable tax terms.

Dimethyl ether can be produced either directly from methanol or indirectly from natural or bio gas. In the latter case, the natural or bio gas is first of all reformed into synthesis gas. Synthesis gas can also be obtained by other methods, for example by pyrolysis of waste materials or biomass. The synthesis gas is then either converted into methanol and then into dimethyl ether in a two-step reaction or converted directly into dimethyl ether in a one-step reaction.

The synthesis of dimethyl ether from synthesis gas has thermodynamic and economic advantages over synthesis from methanol.

The present invention relates in particular to the one-step synthesis of dimethyl ether, the term "one-step" synthesis referring to a method of synthesis in which all the reactions take place in one and the same reactor. The one-step synthesis of dimethyl ether is known for example from U.S. Pat. No. 4,536,485 A and U.S. Pat. No. 5,189,203 A. Conventionally, hybrid catalysts are used. The reaction is exothermic and is typically carried out at a temperature of from 200 to 300° C. at a pressure of 20 to 100 bar.

For the one-step synthesis of dimethyl ether, normally upright tube reactors are used which are charged from below with pressurised, heated synthesis gas. A product stream obtained in the tube reactor is removed from the top, cooled and introduced into a separation.

The product stream contains, in addition to dimethyl ether, unreacted components of the synthesis gas as well as other reaction products. Typically, the product stream comprises, besides dimethyl ether, at least methanol, water, carbon dioxide, carbon monoxide and hydrogen and minor amounts of methane, ethane, organic acids and higher alcohols.

In a gas mixture which is formed from the product stream, besides dimethyl ether there will typically be carbon dioxide and components that are lower-boiling than carbon dioxide, such as hydrogen and carbon monoxide. To obtain dimethyl ether that meets a relevant specification, these other components must be at least partially separated off. Methods used for this have, however, proved unsatisfactory particularly from the point of view of energy.

In order to recover dimethyl ether from the product stream the latter has to be cooled to temperatures significantly below 0° C. It may be necessary to separate off large amounts of methanol and water before cooling. The present invention, however, also discloses methods in which such separation is not needed.

From U.S. Pat. No. 5,908,963 A, a method of producing a dimethyl ether product is known in which from a product stream of a dimethyl ether reactor a condensate containing water and methanol is separated. Dimethyl ether is washed out of the remaining gas phase by methanol obtained from the condensate.

Over all, there is a need for improved methods of processing corresponding gas mixtures by separation technology.

DISCLOSURE OF THE INVENTION

Against this background the present invention proposes a method of separation technology processing of a gas mixture which is formed from a product stream of a reactor for synthesising dimethyl ether from synthesis gas and which contains at least dimethyl ether, carbon dioxide and at least one other component which is lower boiling than carbon dioxide according to the features of the independent claims. Preferred embodiments are recited in the sub-claims and the description that follows.

Before the explanation of the features and advantages of the present invention, their basis and the terminology used will be explained.

A fluid (the term "fluid" is hereinafter also used to refer to corresponding streams, fractions, etc.) is "derived" from another fluid (which is also referred to as the starting fluid) or is "formed" from such a fluid, if it comprises at least some components that were present in the starting fluid or are obtained therefrom. A fluid which is derived or formed in this way may be obtained or formed from the starting fluid by separating off or deriving a fraction or one or more components, concentrating or depleting one or more components, chemically or physically reacting one or more components, heating, cooling, pressurising and the like. A stream may also simply be "formed" for example by being drawn off from a storage container.

Fluids in the terminology used here may be rich or poor in one or more of the components present, "rich" denoting a content of at least 90%, 95%, 99%, 99.5%, 99.9%, 99.99% or 99.999% and "poor" denoting a content of not more than 10%, 5%, 1%, 0.1%, 0.01% or 0.001%, based on weight or volume. In the terminology used here, they may be enriched in or depleted in one or more components, these terms referring to a corresponding content in a starting fluid from which the fluid has been formed. The fluid is "enriched" if it contains at least 1.1 times, 1.5 times, 2 times, 5 times, 10 times, 100 times or 1,000 times the amount, and "depleted" if it contains not more than 0.9 times, 0.5 times, 0.1 times, 0.01 times or 0.001 times the amount of a corresponding component, based on the starting fluid. A fluid "predominantly" containing one or more components contains the one or more component(s) in amounts of at least 90%, 95%, 98% or 99% or is rich in them.

The terms "pressure level" and "temperature level" will be used hereinafter to characterise pressures and temperatures, the intention being to indicate that pressures and temperatures do not have to be used in the form of precise pressure or temperature values in order to implement an inventive concept. However, such pressures and temperatures typically vary within certain ranges which are for example ±1%, 5%, 10%, 20% or even 50% either side of a mean value. Different pressure levels and temperature levels may be located in disjointed ranges or in ranges that overlap. In particular, pressure levels will include unavoidable or expected pressure losses caused, for example, by the effects of cooling. The same is true of temperature levels. The pressure levels given in bar are absolute pressures.

A "distillation column" in the terminology used here is a separating unit which is arranged to at least partially separate a mixture of substances (fluid) provided in gaseous or liquid form or in the form of a two-phase mixture with liquid and gaseous components, optionally also in the supercritical state, i.e. to produce, from the mixture of substances, pure substances or mixtures of substances which are enriched or depleted, or rich or poor, in at least one component compared with the mixture of substances, in the sense described above. Distillation columns are sufficiently known from the field of separation technology. Typically, distillation columns are configured as cylindrical metal containers which are equipped with fittings such as perforated bases or structured or unstructured packing. A distillation column is characterised inter alia in that a liquid fraction separates off at the bottom, also referred to as the sump. This liquid fraction, which is referred to here as a sump liquid, is heated in a distillation column by means of a sump evaporator so that some of the sump liquid is continuously evaporated and rises in gaseous form within the distillation column. A distillation column is also typically provided with a so-called top condenser into which at least some of a gas mixture that is to be enriched in an upper part of the distillation column or a corresponding pure gas, referred to here as the top gas, is fed, partially liquefied to form a condensate and added at the top of the distillation column as a liquid reflux. Some of the condensate obtained from the top gas can be used elsewhere.

In contrast to a distillation column, an "absorption column" typically does not have a sump evaporator. Absorption columns are also generally known from the field of separation technology. Absorption columns are used for absorption in the phase counterflow and are therefore also referred to as counterflow columns. In counterflow absorption, the releasing gas phase flows upwards through an absorption column. The receiving solution phase, added at the top and drawn off at the bottom, flows counter to the gas phase. The gas phase is "washed" with the solution phase. In a corresponding absorption column, fittings are also typically provided which ensure a stepwise phase contact (bases, spray zones, rotating plates, etc.) or constant phase contact (unregulated pouring of fillings, packings, etc.). At the top of an absorption column of this kind, a gaseous fluid is obtained which can be drawn off from the column as a "top product". In the sump of the absorption column a liquid is separated off which can be drawn off as a "sump product". In the absorption column the gas phase is stripped of one or more components which go into the sump product.

For the design and specific configuration of distillation columns and absorption columns reference may be made to textbooks on the subject (cf. for example Sattler, K.: Thermische Trennverfahren: Grundlagen, Auslegung, Apparate, [Thermal separation methods: Principles, Design, Apparatus], $3^{rd}$ edition 2001, Weinheim, Wiley-VCH).

Where reference is hereinafter made to a "synthesis" of dimethyl ether for short, this denotes a method in which a feed containing a synthesis gas, i.e. a gas mixture, which contains at least carbon monoxide and hydrogen in suitable amounts, is reacted to form a corresponding product stream containing dimethyl ether. Because of the incomplete reaction and because of the occurrence of secondary reactions during the synthesis of dimethyl ether, particularly depending on the characteristics of the catalysts used and the respective amounts of the components of the synthesis gas, a corresponding product stream contains not only dimethyl ether but also other compounds. These are, at least, methanol, water, carbon dioxide, carbon monoxide and hydrogen but also, typically, minor amounts of methane, ethane, organic acids and higher alcohols. These additional compounds have to be separated off, as mentioned above. The separation is carried out on the one hand to enable subsequent separation steps and on the other hand to recover dimethyl ether with the required purity, i.e. "in accordance with the specifications".

ADVANTAGES OF THE INVENTION

As already mentioned, the method according to the invention comprises separation technology processing of a gas mixture which is formed from a product stream of a reactor for synthesising dimethyl ether from synthesis gas, and which contains at least dimethyl ether, carbon dioxide and at least one other component which is lower-boiling than carbon dioxide. Such components which are lower-boiling than carbon dioxide may be, in particular, components such as carbon monoxide and hydrogen. As already mentioned, other components which are also lower-boiling than carbon dioxide, such as methane, for example, are also present in minor amounts in a gas mixture of this kind.

A component which is "lower-boiling than carbon dioxide" has a lower boiling point than carbon dioxide. It should be mentioned at this point that at the pressure levels used according to the invention (the "first" pressure level explained hereinafter is above the triple point of carbon dioxide) carbon dioxide may also be present in liquid form.

According to the invention the gas mixture at the first pressure level is cooled from a first temperature level to a second temperature level. This may advantageously be carried out via one or more intermediate temperature levels and with the separation by condensation of one or more condensates from the gas mixture, but one-step cooling is also possible.

If condensates are separated beforehand, these predominantly contain dimethyl ether and carbon dioxide if the gas mixture used is poor in higher boiling components such as methanol and water. For example, the gas mixture may be free or substantially free from methanol and water, as methanol and water are separated off beforehand. An arrangement as shown in FIG. 2 may be used for this, for example. Alternatively, no separation may be done. If no separation is carried out, however, care must be taken to ensure that neither methanol nor water is present on its own in a corresponding gas mixture. Water without an added amount of methanol would freeze at the low temperatures used, as the frost protection effect of the methanol would be absent. Conversely, however, "dry" methanol would also have disadvantages as it could damage the heat exchangers used.

A fraction of the gas mixture remaining in gaseous form at the second temperature level is washed in an absorption column with a reflux predominantly containing carbon dioxide, thus obtaining a top product and a sump product. This serves to wash any dimethyl ether still contained in the fraction of the gas mixture that is still gaseous into the sump product, so that the top product is as free from dimethyl ether as possible. The top product consists predominantly of carbon dioxide and the at least one component which is lower-boiling than carbon dioxide at the first pressure level. The top product preferably contains no dimethyl ether or at most only small amounts and is thus at least poor in dimethyl ether in the sense described above.

The reflux predominantly containing carbon dioxide is formed, according to the invention, from a fraction of the gas mixture which has been separated off in liquid form during cooling to the second temperature level. Preferably, a dimethyl ether/carbon dioxide distillation column is used for this. If one or more condensates are separated during the cooling, these condensates, or streams formed from them, are preferably at least partially fed into the dimethyl ether/carbon dioxide distillation column. A sump product from the absorption column or a stream formed from it can also be at least partially fed into the dimethyl ether/carbon dioxide distillation column.

By a "dimethyl ether/carbon dioxide distillation column" is meant here a distillation column which is configured and operated such that fluids which are enriched in dimethyl ether on the one hand and carbon dioxide on the other hand and are depleted in the other component in each case can be recovered in said column from fluids containing dimethyl ether and carbon dioxide. The skilled man chooses the specific configuration of a dimethyl ether/carbon dioxide distillation column (such as the type and number of fittings, for example) and the operating conditions (such as the operating pressure, heating and cooling fluids in the sump evaporator and top condenser, for example) particularly on the basis of the difference in boiling points of dimethyl ether and carbon dioxide.

An essential aspect of the present invention is the suitable adjustment of the operating conditions of the dimethyl ether/carbon dioxide distillation column. These are advantageously chosen such that a top gas predominantly containing carbon dioxide which is drawn off from the top of the dimethyl ether/carbon dioxide distillation column can be liquefied above the melting temperature of carbon dioxide. A correspondingly obtained condensate should be available in a sufficient quantity to be used as a reflux for the dimethyl ether/carbon dioxide distillation column, on the one hand, and to be available as a reflux for an absorption column, on the other hand, as already partly explained.

Advantageously, the dimethyl ether/carbon dioxide distillation column is operated such that a top gas predominantly containing carbon dioxide is formed at its top and a sump liquid high in dimethyl ether is formed at its bottom. The sump liquid predominantly contains dimethyl ether if the fluids fed into the dimethyl ether/carbon dioxide distillation column (for example, the condensate(s) mentioned previously and the sump product from the absorption column) predominantly contain carbon dioxide and dimethyl ether. If the latter also contain water and methanol, these also pass into the sump liquid of the dimethyl ether/carbon dioxide distillation column.

Thus, by using the carbon dioxide-rich liquid reflux on the absorption column the invention makes it possible to reduce the losses of dimethyl ether. Part of the condensate which is formed from at least some of the top gas from the dimethyl ether/carbon dioxide distillation column is used as the reflux predominantly containing carbon dioxide. At the sump end, the liquid sump product mentioned previously, which may consist predominantly of dimethyl ether and carbon dioxide (and optionally also contains water and methanol), is removed from the absorption column. Preferably, this sump product contains all the dimethyl ether which has been fed into the absorption column, or the majority thereof.

Cooling to the second temperature level is advantageously carried out by the use of available refrigerants such as C3 or also C2 refrigerants (e.g. liquid propane or ethane or equivalents, for achieving a corresponding temperature). Previous stepwise cooling to intermediate temperature levels, if carried out, is accomplished for example with water and/or a C3 refrigerant (e.g. liquid propane or an equivalent). The first temperature level is advantageously 20 to 50° C., particularly 30 to 40° C. The first temperature level may also be 50 to 150° C., particularly 70 to 120° C., for example 80 to 100° C. or, in relation to the dew point, for example, at least 10° C. and not more than 30 to 50° C. above the dew point. The second temperature level is advantageously between the melting temperature of carbon dioxide at the pressure level used and −15° C., for example at −40° C. to −20° C. and particularly at about −35° C., the temperature of a C3 refrigerant. The temperature level may also be just above, i.e. at least 0.5 to 10° C., particularly 1 to 5° C. above, the melting temperature of carbon dioxide at the pressure level used. The temperature level used also depends on the composition of the cooled gas mixture and the desired composition of the condensates separated. Since the carbon dioxide-rich reflux is obtained from corresponding condensates within the scope of the present invention, the temperature level is selected such that the condensates contain at least sufficient carbon dioxide. The carbon dioxide content is sufficient when, during the separation of condensates in the dimethyl ether/carbon dioxide distillation column, enough carbon dioxide is obtained at the top of the column to enable a sufficiently liquid reflux to be deposited on the dimethyl ether/carbon dioxide distillation column and a sufficiently liquid reflux to be deposited on the absorption column.

The method proposed according to the invention has proved more favourable in energy terms than conventional methods, with the result that the measures according to the invention achieve advantageous separation compared with separation methods known from the prior art.

The present invention is particularly suitable for methods in which the product stream from the reactor used to synthesise dimethyl ether from synthesis gas is provided at a pressure level of 20 to 100 bar, particularly at a pressure level of 30 to 80 bar (the "first pressure level"). The product stream can be substantially freed from methanol and water at this first pressure level, using another absorption column. The separation of methanol and/or water can thus take place under pressure and there is no need for a release of pressure beforehand, which would then require pressurisation to be repeated, with associated energy costs. The gas mixture obtained from the product stream is thus not depressurised after leaving the reactor for the synthesis of dimethyl ether and before the separation process according to the invention. Re-compression with high energy consumption is therefore not required.

The present invention is suitable for separation immediately following the synthesis and any subsequent cooling and/or elimination of water and/or methanol. During this separation the product stream is at the first temperature level.

The method according to the invention can be used with product streams of a wide range of compositions. Corresponding product streams contain for example 2 to 50 mol %, particularly 5 to 30 mol % of dimethyl ether, 0.1 to 20 mol %, particularly 0.7 to 10 mol % of methanol, 0.1 to 20 mol %, particularly 0.8 to 10 mol % of water, 1 to 50 mol %, particularly 3 to 30 mol % of carbon dioxide, 0.1 to 25 mol %, particularly 1 to 11 mol % of carbon dioxide and 5 to 90 mol %, particularly 20 to 80 mol % of hydrogen. If elimination of water and methanol is carried out, the gas mixture is preferably poor in water and methanol.

Corresponding product streams may also contain minor amounts of other components, such as methane, ethane, organic acids and higher alcohols, as mentioned. Corresponding mixtures are obtained particularly in processes in which a one-step synthesis of dimethyl ether is carried out.

As already mentioned, the dimethyl ether/carbon dioxide distillation column within the scope of the present invention is advantageously operated such that a top gas predominantly containing carbon dioxide which is drawn off from the top of the dimethyl ether/carbon dioxide distillation column can be liquefied above the melting temperature of carbon dioxide. The dimethyl ether/carbon dioxide distillation column is advantageously operated at a second pressure level which is below the first pressure level. The second pressure level is selected so that carbon dioxide can be condensed from the top gas as much as possible using available refrigerants. The temperature of these refrigerants is typically −52° C. to −20° C., for example −35° C. (C3 refrigerant). If the gas mixture used is poor in methanol and water or if methanol and water have been separated off, the sump liquid can be taken from the dimethyl ether/carbon dioxide distillation column as a stream rich in dimethyl ether, having a dimethyl ether content of at least 90 mol %, particularly at least 95 mol % or at least 99 mol %. The respective contents depend on the operating conditions of the dimethyl ether/carbon dioxide distillation column and its configuration. They may be adapted to the required specification (purity) of a product stream obtained accordingly. If, on the other hand, the gas mixture contains methanol and water to an appreciable degree and/or if there is no separation of methanol and water, methanol and water are present in the sump liquid.

As already mentioned, the liquid reflux which is added to the absorption column consists predominantly of carbon dioxide. Advantageous carbon dioxide contents are at least 90 mol %, for example, especially at least 95 mol % or at least 99 mol %.

The method makes it possible to reduce the losses of dimethyl ether in the final condensation column by using the absorption column. The liquid reflux onto the absorption column, this reflux predominantly containing carbon dioxide formed from the top gas of the dimethyl ether/carbon dioxide distillation column, advantageously has a dimethyl ether content of not more than 10 mol %, particularly at most 5 mol %, at most 1 mol % or at most 0.5 mol %. Corresponding contents may also be obtained in the top stream of the absorption column.

The invention is explained more fully with reference to the drawings, which show an embodiment of the invention by comparison with the prior art.

DETAILED DESCRIPTION OF THE DRAWINGS

Figure 1:
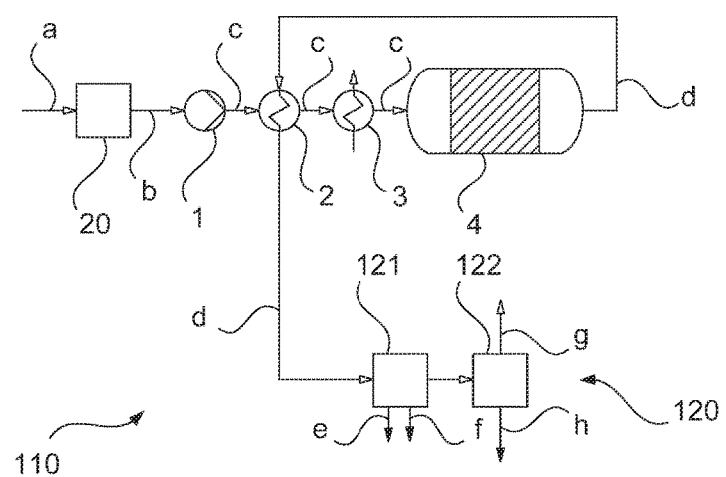
FIG. 1 shows an apparatus for producing dimethyl ether according to the prior art, in schematic representation.

In the Figures, elements that correspond to one another have been given identical reference numerals and are not described again, for the sake of clarity.

FIG. 1 schematically shows an apparatus for producing dimethyl ether according to the prior art, which is generally designated 110.

The apparatus 110 comprises a synthesis gas reactor 20, shown in highly schematic form, which can be charged with a suitable feed a, such as natural or bio gas, for example. A synthesis gas stream b can be removed from the synthesis gas reactor 20.

The synthesis gas stream b can be put under increased pressure by means of a compressor 1, optionally after the addition of other streams. In this way, the pressure required for a subsequent one-step synthesis of dimethyl ether, for example a pressure of 20 to 100 bar, can be applied.

A correspondingly compressed stream, now designated c, is passed through a first heat exchanger 2 which can be heated with a product stream d of a reactor 4 for synthesising dimethyl ether (see below). The correspondingly heated stream, still designated c, has a temperature of 200 to 300° C., for example, downstream of the first heat exchanger 2. The stream c is optionally passed through a second heat exchanger 3, which is also referred to as a peak heater.

The stream subjected to further heating in the second heat exchanger 3, and still designated c, is fed into the reactor 4, which is configured as a tube reactor and the reaction tubes of which are filled with a suitable catalyst for the one-step synthesis of dimethyl ether. The representation in FIG. 1 is highly simplified. Typically, reactors 4 for synthesising dimethyl ether are arranged vertically, with a stream c being fed into the tube reactor 4 at the bottom. A stream d is removed from the reactor 4 at the top.

As a result of the exothermic reaction in the tube reactor 4, the stream d is at an even higher temperature. The stream d is passed as a heating medium through the heat exchanger 2. As a result, it cools to a temperature which is for example about 30° C. above the temperature of the stream c downstream of the compressor 1. The correspondingly cooled stream, still designated d, is fed into a conventional separation apparatus 120. In the separation apparatus 120, a methanol stream e and a water stream f are separated from the stream d, for example with intermediate pressure release, cooling, re-compression, etc. (not shown) in one step 121. From the residue remaining, the streams g and h are formed, which may be for example a stream g enriched in carbon dioxide and a stream h enriched in dimethyl ether.

The composition of the streams g and h depends, inter alia, on the composition of the stream d and the specific configuration and the operating parameters of the separation apparatus 120.

Figure 2:
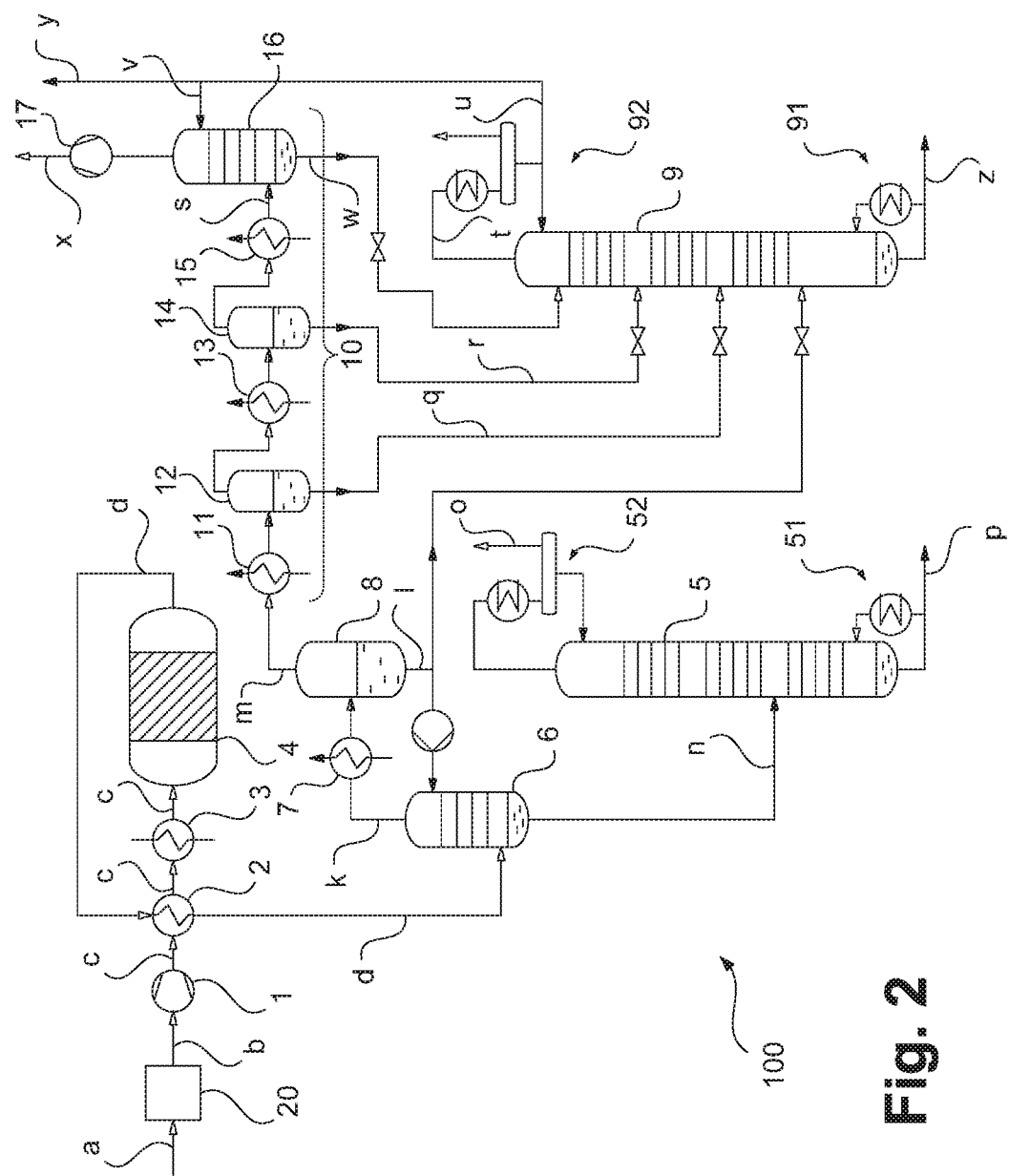
FIG. 2 shows an apparatus for producing dimethyl ether according to one embodiment of the invention, in schematic representation.

FIG. 2 shows an apparatus for producing dimethyl ether according to one embodiment of the invention. This is generally designated 100.

A first absorption column which is used to separate methanol and/or water is designated 6 in FIG. 2. As already explained, an absorption column 6 differs from a distillation column such as the distillation column 5 (see below) inter alia in that it does not have a sump evaporator. Vapours rising in the absorption column 6 are washed by a reflux added at the top of the absorption column 6, so that the more volatile components are concentrated at the top of the absorption column 6 and the less volatile components are concentrated in the sump of the absorption column 6.

In the apparatus 100, which is shown in FIG. 2, the stream d is introduced into the absorption column 6. A top stream k is drawn off from the top of the absorption column 6 and cooled in a heat exchanger 7 against a suitable refrigerant, such as coolant water, for example. The correspondingly cooled stream k is transferred into a separation container 8, from the sump of which a liquid stream l is taken and added to the absorption column 6 by means of a pump (not marked) at least partly as a reflux.

If, in addition to dimethyl ether, the stream d in the embodiment shown contains methanol, water, carbon dioxide, carbon monoxide and hydrogen (together with traces of other compounds as explained above), dimethyl ether, carbon dioxide, carbon monoxide and hydrogen pass into the top stream k from here, as a result of the backwash described. As a result of suitable cooling in the heat exchanger 7 and corresponding separation conditions in the separation container 8, a sump product is separated in the separation container 8, consisting essentially of dimethyl ether and carbon dioxide (possibly with traces of methanol).

From the top of the separation container 8, a gaseous stream m, which still contains dimethyl ether in addition to carbon dioxide, carbon monoxide and hydrogen, can be drawn off. The stream m is then subjected to sequential cooling and condensation, as described hereinafter. The part of the stream l which is not added to the absorption column 6 as a liquid reflux is fed into a distillation column 9, referred to here as a dimethyl ether/carbon dioxide distillation column, like the condensates occurring in the sequential cooling and condensation of the stream m.

It should be expressly pointed out that the specific preparation of the stream k, which is obtained from the product stream d, need not take place in the manner shown. Other possible ways of separating water and/or methanol may be used, provided that they lead to the production of a gas mixture at the above-mentioned first pressure level and the first temperature level and containing the stated amounts of the individual components.

The invention can also be carried out without any separation of water and methanol. In this case care must be taken to ensure that, for the reasons stated above, both water and methanol are present in the gas mixture that is to be cooled, in order to make use of the frost protection effect of methanol and prevent the corrosive effect of dry methanol.

A liquid stream n is taken from the sump of the absorption column 6 and fed into a distillation column 5 at a suitable height, the distillation column being operated with a sump evaporator 51 and a top condenser 52. The stream n in the embodiment shown contains the great majority of the water and methanol contained in the stream d.

The sump evaporator 51 and the top condenser 52 are operated with suitable heating and cooling means, respectively, preferably contained in a corresponding apparatus. In the sump evaporator 51, a liquid stream drawn off from the sump of the distillation column 5 is partially evaporated and fed into a lower region of the distillation column 5. An unevaporated fraction can be drawn off as stream p.

From the top of the distillation column 5, a gaseous stream is drawn off, partially liquefied in the top condenser 52 of the distillation column 5 and fed into the distillation column 5 again in an upper region as a liquid reflux. A fraction o remaining in gaseous form is drawn off.

Thus, in the distillation column 5, from the stream n which essentially still contains water, methanol, hydrogen, dimethyl ether and carbon dioxide are formed a stream (stream o) essentially containing dimethyl ether and carbon dioxide and a stream (stream p) essentially containing methanol and water. The stream o may be recycled into the separation process at a suitable point. The stream p can be used elsewhere. Any water separated off can also be fed into waste water treatment or degassing.

The reflux quantity and number of plates in the absorption column 6 can be optimised so that a corresponding sump product n is obtained in as small a quantity as possible. Advantageously, the reflux which is added to the absorption column 6 as part of the stream l is adjusted so as to minimise the content of methanol and water in the stream k. The composition of the stream m thus obtained is such that in the cooling and condensation sequence to which the stream m is subjected the disadvantages mentioned previously cannot arise.

The steps, mentioned several times previously, for further treatment of the stream m are generally designated 10 here. The stream m is first fed into a heat exchanger 11 and then into a separation container 12. The cooling in the heat exchanger 11 is carried out so that a first condensate q is separated in the separation container 12. A fraction remaining in gaseous form in the separation container 12 is fed into a heat exchanger 13 and then into another separation container 14. Here, too, a condensate, designated r, is obtained.

The condensates q and r are fed, together with the fraction of the stream l which has not been recycled into the absorption column 6, into the dimethyl ether/carbon dioxide distillation column 9 mentioned previously, which is operated as explained hereinafter.

A fraction remaining in gaseous form at the top of the separation container 14 is cooled in another heat exchanger 15. It is present downstream of the heat exchanger 15 at the "second" temperature level described several times hereinbefore, between the melting point of carbon dioxide (at the prevailing pressure) and −15° C. The temperature of the stream m upstream of the heat exchanger 11 (i.e. the "first" temperature level) is +35° C., by contrast. The correspondingly cooled stream, here designated s, is transferred into an absorption column 16 which may be operated according to the invention.

The invention may also be used in a highly simplified arrangement, for example with one-step cooling and with no separation of methanol and water. However, a fraction of the gas mixture remaining in gaseous form at the second temperature level is washed, in an absorption column 16, with a reflux predominantly containing carbon dioxide, as explained hereinafter. The reflux predominantly containing carbon dioxide is formed from a liquid fraction of the gas mixture separated during cooling.

The stream s in the embodiment shown still contains dimethyl ether, carbon dioxide, carbon monoxide and hydrogen, i.e., in addition to dimethyl ether and carbon dioxide, two components which are lower-boiling than dimethyl ether. Using a liquid reflux v which is rich in carbon dioxide and is formed from a part of a condensate u which is obtained from a top stream t comprising a top gas of the dimethyl ether/carbon dioxide distillation column 9, a mixture of dimethyl ether and carbon dioxide is separated in the sump of the absorption column 16 and drawn off in the form of the sump product w. The sump product w may also be fed into the dimethyl ether/carbon dioxide distillation column 9. At the top of the absorption column 16, by contrast, a top product x is drawn off, which consists essentially of carbon dioxide, carbon monoxide and hydrogen and is poor in or preferably free from dimethyl ether. This may be used elsewhere, optionally after being suitably compressed in a compressor 17.

As already mentioned, the fraction of the stream l which has not been recycled into the absorption column 6, as well as the streams q and r and the sump product w, are fed into the dimethyl ether/carbon dioxide distillation column 9. As they contain different amounts of dimethyl ether and carbon dioxide (traces of carbon monoxide and hydrogen are also present in dissolved form), they are fed into the dimethyl ether/carbon dioxide distillation column 9 at different heights, for which purpose suitable valves (not shown) are provided.

The dimethyl ether/carbon dioxide distillation column 9 is also operated with a sump evaporator 91 and a top condenser 92. A top stream t formed from a top gas of the dimethyl ether/carbon dioxide distillation column 9 is at least partially liquefied in the top condenser 92 using a heat exchanger operated with a suitable refrigerant and is added as a liquid reflux to the dimethyl ether/carbon dioxide distillation column 9. Another fraction u is used to form the reflux v and another stream y, which may be used elsewhere.

From the sump of the dimethyl ether/carbon dioxide distillation column 9 is taken a liquid stream z which consists essentially of dimethyl ether in this case but is, in particular, free from or poor in carbon dioxide.

The invention claimed is:

1. Method for the processing, by separation technology, of a gas mixture (k) which is formed from a product stream (d) of a reactor (4) for synthesising dimethyl ether from synthesis gas (b), and which contains at least dimethyl ether, carbon dioxide and at least one other component which is lower-boiling than carbon dioxide, characterised in that the gas mixture (k) at a first pressure level is cooled from a first temperature level to a second temperature level and a fraction of the gas mixture (k) that remains in gaseous form at the second temperature level is washed in an absorption column (16) with a reflux (v) predominantly containing carbon dioxide, the reflux (v) predominantly containing carbon dioxide being at least partially formed from a fraction of the gas mixture (k) which is separated in liquid form during the cooling.

2. Method according to claim 1, wherein the gas mixture (k) is cooled through several intermediate temperature levels to the second temperature level, in the course of which a plurality of condensates (l, q, r) are separated.

3. Method according to claim 1, wherein the fraction of the gas mixture (k) remaining in gaseous form at the second temperature level is washed in an absorption column (16) with the reflux (v) predominantly containing carbon dioxide, in the course of which a top product (x) and a sump product (w) are recovered, the reflux (v) which predominantly contains carbon dioxide being formed partially from the sump product (w).

4. Method according to claim 1, wherein the reflux (v) predominantly containing carbon dioxide is formed using a dimethyl ether/carbon dioxide distillation column (9).

5. Method according to claim 4, wherein the dimethyl ether/carbon dioxide distillation column (9) is operated such that at its top is formed a top gas (t) predominantly containing carbon dioxide and in its sump is formed a sump liquid rich in dimethyl ether.

6. Method according to claim 5, wherein part of a condensate which is formed from at least part of the top gas of the dimethyl ether/carbon dioxide distillation column (9) is used as the reflux (v) predominantly containing carbon dioxide.

7. Method according to claim 5, wherein at least some of the sump liquid of the dimethyl ether/carbon dioxide distillation column (9) is drawn off as a product stream (z) which has a dimethyl ether content of more than 90 mol %.

8. Method according to claim 4, wherein the dimethyl ether/carbon dioxide distillation column (9) is operated at a second pressure level which is below the first pressure level.

9. Method according to claim 1, wherein the reflux predominantly containing carbon dioxide has a dimethyl ether content of not more than 10 mol %.

10. Method according to claim 1, wherein the gas mixture (k) is formed by at least partially removing methanol and/or water from the product stream (d).

11. Method according to claim 1, wherein the first temperature level is 20 to 50° C., and wherein the second temperature level is between the melting temperature of carbon dioxide at the pressure level used and −15° C.

12. Method according to claim 1, wherein the first pressure level is 20 to 100 bar.

* * * * *